United States Patent
Rongen et al.

(10) Patent No.: US 8,000,507 B2
(45) Date of Patent: Aug. 16, 2011

(54) VIEWING SYSTEM FOR CONTROL OF PTCA ANGIOGRAMS

(75) Inventors: Peter Maria Johannes Rongen, Eindhoven (NL); Raoul Florent, Ville d'Avray (FR); Herman Stegehuis, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 1055 days.

(21) Appl. No.: 11/568,273

(22) PCT Filed: Apr. 26, 2005

(86) PCT No.: PCT/IB2005/051354
§ 371 (c)(1),
(2), (4) Date: Jul. 25, 2007

(87) PCT Pub. No.: WO2005/104951
PCT Pub. Date: Nov. 10, 2005

(65) Prior Publication Data
US 2008/0045827 A1    Feb. 21, 2008

(30) Foreign Application Priority Data
Apr. 29, 2004    (EP) .................................... 04300250

(51) Int. Cl.
*G06K 9/00*    (2006.01)
*A61B 5/05*    (2006.01)
(52) U.S. Cl. ......... 382/128; 382/190; 382/254; 600/407
(58) Field of Classification Search .......... 382/128–134, 382/164, 171, 177, 173, 154, 190, 254; 378/191, 378/164, 34; 345/424, 426, 581; 600/403, 600/411, 424–425
See application file for complete search history.

(56) References Cited

U.S. PATENT DOCUMENTS

| | | | | |
|---|---|---|---|---|
| 5,050,855 A | * | 9/1991 | Focke et al. | 271/132 |
| 5,896,463 A | * | 4/1999 | Kuhn | 382/133 |
| 6,532,380 B1 | * | 3/2003 | Close et al. | 600/431 |
| 7,155,045 B2 | * | 12/2006 | Rick et al. | 382/130 |
| 7,415,169 B2 | * | 8/2008 | Florent et al. | 382/294 |
| 7,426,256 B2 | * | 9/2008 | Rasche et al. | 378/8 |
| 7,844,126 B2 | * | 11/2010 | Mory et al. | 382/254 |

FOREIGN PATENT DOCUMENTS

| | | |
|---|---|---|
| WO | 03045263 A2 | 6/2003 |
| WO | 03049032 A2 | 6/2003 |

OTHER PUBLICATIONS

Ioannis Kompatsiaris et al; "Deformable Boundary Detection of Stents in Angiographic Images", IEEE Transactions on Medical Imaging, vol. 19, No. 6, Jun. 2000.
ISR: PCT/IB05/051354.
Written Opinion: PCT/IB05/051354.

* cited by examiner

*Primary Examiner* — Daniel G Mariam
*Assistant Examiner* — Nancy Bitar

(57) ABSTRACT

A medical viewing system for processing and displaying a sequence of medical angiograms representing a balloon, moving in an artery, this system comprising extracting means for automatically extracting balloon image data in a phase of balloon expansion, and computing means for automatically defining and storing coordinates of a Region of Interest (ROI) based on the expanded balloon image data, located around the expanded balloon; and display means for displaying the images. Contrast agent may be used as agent of balloon expansion. The system may have means to detect and keep track of balloon markers and means to look around those markers for further balloon image data extraction.

17 Claims, 7 Drawing Sheets

VIEWING SYSTEM FOR CONTROL OF PTCA ANGIOGRAMS

FIELD OF THE INVENTION

The invention relates to a medical viewing system having means for detecting objects of interest in a sequence of medical images. The invention particularly relates to a viewing system, which has image processing means and image display means, for accurate control of the positioning of medical tools in an artery, in a sequence of angiograms. The invention finds for example its application for accurate control of the positioning of a stent in a coronary in an operation of "Percutaneous Transluminal Coronary Angioplasty" (PTCA). The invention also relates to an image processing method to be used in said system. The invention further relates to a medical examination apparatus coupled to such a system.

BACKGROUND OF THE INVENTION

A method for extracting stents in medical images is already known from the publication entitled "Deformable Boundary Detection of Stents in Angiographic Images", by Ioannis Kompatsiaris et alii, in IEEE TRANSACTIONS ON MEDICAL IMAGING, VOL. 19, No. 6, JUNE 2000, pages 652-662. This document describes an image processing method for deformable boundary detection of medical tools, called stents, in angiographic images. A stent is a surgical stainless steel coil that is placed in a coronary in order to improve blood circulation in regions where a stenosis has appeared. A stenosis is a narrowing of the coronary. When a stenosis is identified in a coronary of a patient, a procedure Percutaneous Transluminal Coronary Angioplasty (PTCA) may be prescribed. A basic idea of PTCA is to position a monorail with a small inflatable balloon within the narrowed section of the coronary. The balloon is inflated in order to push outwards the wall of the narrowed coronary. This process reduces the narrowing until it no longer interferes with the blood flow. The balloon is then deflated and removed from the coronary. In order to avoid re-stenosis to occur in the previously stenosed region of the coronary, said process is often followed by a stent implantation performed in said region. The stent is introduced in the coronary using another balloon monorail. The stent is wrapped tightly around the second balloon attached to the monorail. Once this second balloon tipped monorail is positioned into said region of the coronary, the balloon is inflated. The deployment of the balloon causes the stent to expand, pressing it against the coronary wall. Then, the balloon and monorail are removed, while the stent, once expanded, can be considered as a permanent implant. This stent acts like a scaffold keeping the coronary lumen open and allowing normal blood flow to occur through the coronary. Stent placement helps many patients avoid emergency heart bypass interventions and/or heart attacks.

The method that is disclosed in the cited publication is focused on visibility of the stent after stent deployment in the angiographic images. It comprises the steps of forming 3D models of stents; deriving a set of 2D models using perspective rules; matching said 2D models with real angiographic images in a training phase; roughly detecting a stent in an angiographic image using the set of 2D models and maximum likelihood criteria; refining the borders of the roughly detected stent using an active contour model.

A drawback of said method is that the calculation load is too heavy for real time processing of a sequence of images in the intervention phase of stent implantation. Another drawback is that it does not provide the robustness and accuracy now required for stent implantation, as checked in a control step of stent positioning.

SUMMARY OF THE INVENTION

The artery walls, the guide-wire and the stent are mainly radio-transparent. Contrast agent may be diffuse through the coronary in order to visualize and localize the stenosed part of the coronary. When used, contrast agent must be introduced only in very small quantity during very small time duration because it presents toxicity for the patient. So, using contrast agent provides an improved visualization of the artery only during about a dozen of seconds. Besides, the contrast agent only permits of improving the visibility of the coronary, but does not permit of improving the visibility of the balloon or the stent.

Indeed, this step of positioning the stent is a very difficult step, due to bad condition of imaging. The doctor can only follow the intervention on a screen, since, in this intervention, the rib cage of the patient is not open. The guide-wire for the angioplasty is generally introduced through an opening in the femoral artery and pushed through the aorta until the aortic cross towards the Ostium (heart left ventricle). Beyond the aortic cross, the guide-wire is introduced into the coronary that has been diagnosed as suffering of a stenosis. The guide-wire is used to introduce in the stenosed coronary a monorail equipped with a balloon or with a stent wrapped around a balloon. Not only are the monorail, the balloon, the stent and the stenosed artery walls observed in noisy fluoroscopic images, but also they show low radiographic contrast that makes their visualization very difficult. Besides, during this angioplasty intervention, the monorail, equipped with the balloon alone or with the balloon and the stent, is moving with respect to the coronary, the coronary is moving under the influence of the cardiac pulses, and said coronary is seen on a background that is moving under the influence of patient's breathing and heart beats. These movements make identification and localization of the balloon and the stent, which are Objects of Interest (OI) in fluoroscopic images, still more difficult to perform. Moreover, these movements make zooming inefficient because the Objects of Interest may get out of the zoomed image frame.

So, it is an object of the present invention to propose an imaging system having automatic image processing means for automatically defining a Region Of Interest (ROI) based on detection of balloons, in order to minimize user interaction with the viewing system, which minimizes PTCA time duration. According to the invention, this problem is solved by an imaging system having means as recited in Claim 1.

It is another object of the invention to propose such an imaging system having automatic image processing means for registering and enhancing Objects of Interest (OI), in the automatic ROI, in order to improve detection of stent positioning and stent expansion, during PTCA, as further checked using stent control means. The processing means of the invention can be applied on-line i.e. in real time during PTCA, or off-line on a workstation. Specific embodiments of this imaging system are claimed in dependent Claims. An image processing method to be used in the system, a program product to implement the steps of this method and an examination apparatus for helping visualization of interventions having such a system are further claimed.

LIST OF DRAWINGS

Embodiments of the invention are described hereafter in detail in reference to diagrammatic figures wherein.

DESCRIPTION OF EMBODIMENTS

The invention relates to a real time viewing system, which has image processing means, for acquiring a sequence of noisy images and for on-line or off-line automatic definition of a ROI in the images of the sequence, based on automatic detection of structures in the images.

The invention further relates to the application of this automatic ROI to image processing means for registration of Objects of Interest, based on localization of specific structures of the ROI. The invention further relates to the application of this registered automatic ROI to image processing means for enhancement and occasionally zooming of the Objects of Interest in the ROI. The image processing means can be applied off-line. The viewing system and the image processing method of the invention are described hereafter in an example of application to the medical field of cardiology. In this application, the Objects of Interest (OI) are stent implantation tools such as balloons, balloon markers or stents, in a stenosed region of a coronary. They are observed during a medical intervention called Percutaneous Transluminal Coronary Angioplasty (PTCA), in sequences of x-ray fluoroscopic images called angiograms, using low x-ray doses, whose images are very noisy. In fact, PTCA is recorded in several short sequences during short time durations of application of x-rays, in order to minimize patient's irradiation as well as doctors' irradiation.

The user of the viewing system can have the possibility to intervene on the viewing system at each phase of the PTCA. The user has at his disposal control means 68, shown in FIG. 8, to activate and control the image processing means. These control means comprises starting and stopping means for the user to control the duration of the processing operation. The processing means are user-actuated while not moving the tool or tools. It is an object of the invention to minimize the number of user interactions in order to minimize the duration of PTCA.

Figure 1A:
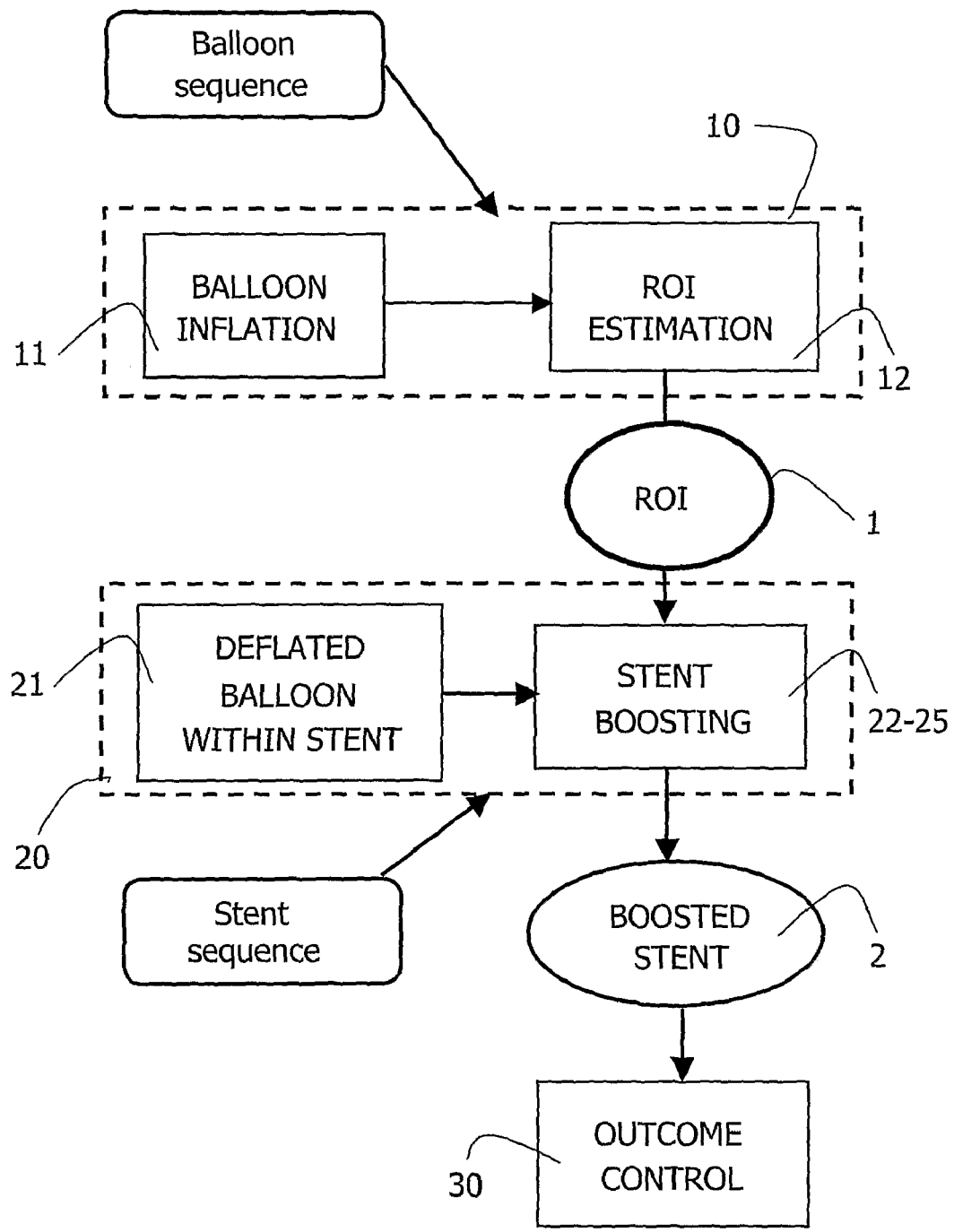
FIG. 1A and FIG. 1B are functional block diagrams of means of the system.

As illustrated by FIG. 1A, at the first stage of PTCA, recorded in a first sequence of images 10, referred to as "Balloon Sequence", a first balloon, attached to a first guided monorail, is positioned in step 11, in the coronary. A region of interest denoted by ROI in the images, must be automatically defined. In effect, it is an object of the invention to provide automatic means to avoid an interactive step of definition of the ROI by the user. The ROI definition means comprises automatic means to detect the more or less radio-transparent balloon associated to the monorail. Detection of the balloon is performed in un-registered images, at a stage of balloon expansion 11, recorded in a first sequence of images 10 comprising at least one image, referred to as "Balloon Sequence".

The balloon may be detected directly. But preferably, the material used for balloon inflation 11 at this stage is a contrast agent. The envelope of the balloon limits contrast agent diffusion, so that said contrast agent does not perfuse through the coronary. The balloon inflated with contrast agent, which is radio-opaque, is therefore more easily identified and localized without ambiguity than when detected without contrast agent. The balloon with contrast agent can be even easily detected when it moves under the influence of the different sources of motions than without contrast agent. At this stage of balloon expansion, a Region Of Interest (ROI) 1, which is limited to a restricted region around the detected balloon, is then automatically estimated in 12. This ROI is defined by co-ordinates and stored for further use.

At the further stage of stent implantation, recorded in a second sequence of images 20, referred to as "Stent Sequence", a second balloon, wrapped by a stent, is now positioned, in step 21, in the coronary. The zone of this second balloon is examined in the automatic ROI 1 previously defined in the "Balloon Sequence" 10.

Figure 1B:
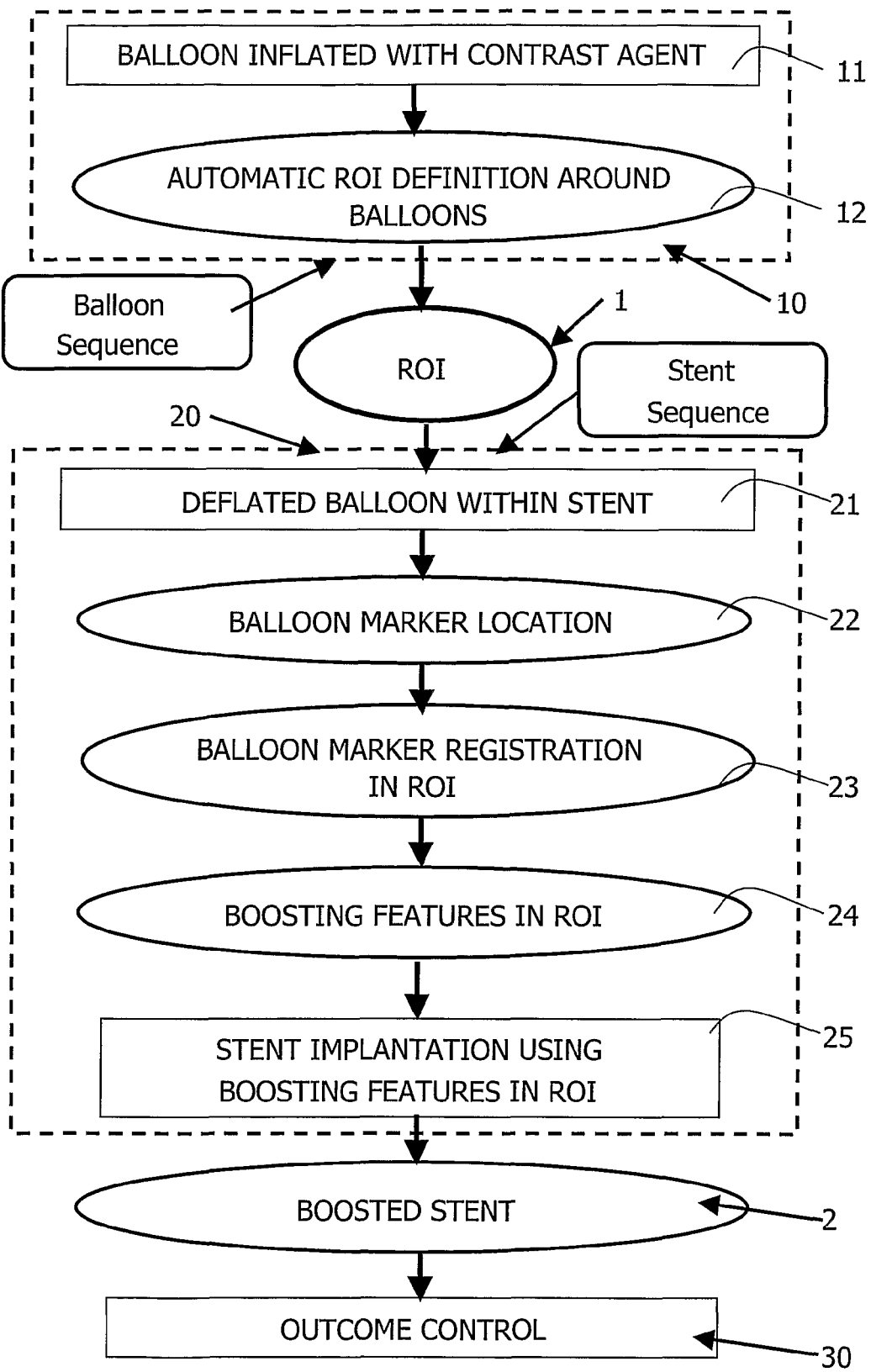

As illustrated by FIG. 1B, balloon markers, which are normally disposed at each extremity of the balloon, are looked for. They are Objects of Interest to be used for ROI registration. These balloon-markers look like small blobs that are radio opaque.

The importance of ROI determination lies in the fact that the actual balloon markers are more easily identified in this ROI than in the entire images. Since the balloon-markers are associated to a balloon that is more or less radio-transparent, in entire images, said balloon-markers could be mistaken with a quantity of details of the background in these very noisy fluoroscopic images. Instead, the definition of the ROI according to the invention permits of eliminating false alarms constituted by other blobs, now outside the ROI, in the un-registered images. The small blobs in the ROI can be clearly identified as balloon markers and extracted without ambiguity.

In the "Stent Sequence" 20, the detected balloon markers are registered in the ROI, which permits of registering the Objects of Interest, based on balloon marker registration. Then, image processing means, called "Stent Boosting" means 22-25, for filtering the background, and for enhancing and occasionally zooming the Objects of Interest are applied to the registered Stent Sequence, which permits of accurately positioning the stent, as further checked in "Outcome Control" procedure 30 of stent localization and expansion.

As illustrated by FIG. 1B, according to the invention, the definition of the ROI is not performed by interactive action of the user. Instead, in order to provide improved assistance to the user, and in order to minimize the duration of PTCA, the system of the invention has means 12 to automatically define this ROI, thus avoiding said interactive step. The automatic detection of ROI is based on previous automatic detection of the radio-opaque balloon in the phase of balloon inflation 11, with contrast agent, in the "Balloon Sequence" 10. Once the balloon is identified, the ROI is automatically defined without user's assistance. Said ROI is defined by co-ordinates. This ROI is defined as the smallest zone comprising the detected balloon at least in one frame or preferably in several frames. The ROI is recorded and stored and further used in the "Stent Sequence" 20.

In the "Stent Sequence" 20, the processing means comprise ROI registration means 21, 22, 23. In the ROI, the balloon being still deflated in step 21, the balloon marker's location is looked for, in step 22, in the restricted ROI now transported into the original images of this "Stent Sequence". It is taken advantage of the fact that, before registration of the images of the sequence, the balloon markers move together in tight correspondence since they are both attached to the balloon. This is a clue to identify the balloon markers in the small ROI. So, the balloon markers can be identified. The balloon markers are extracted and registered in step 23, with respect to the ROI boundaries. Hence, the Objects of Interest (OI), such as the balloon and the stent, can be registered in the ROI, then spatially and temporally filtered and further enhanced and occasionally zoomed.

Among advantages of the invention, the system provides:
- elimination of inaccuracy of balloon marker detection, represented otherwise by about 10% of false alarms;
- accurate and robust result of stent positioning and deployment during PTCA, as checked in "Outcome Control" 30;
- ROI automatic definition without interaction of the user, which minimizes the time duration of PTCA and increases the user's comfort.

Figure 4A:
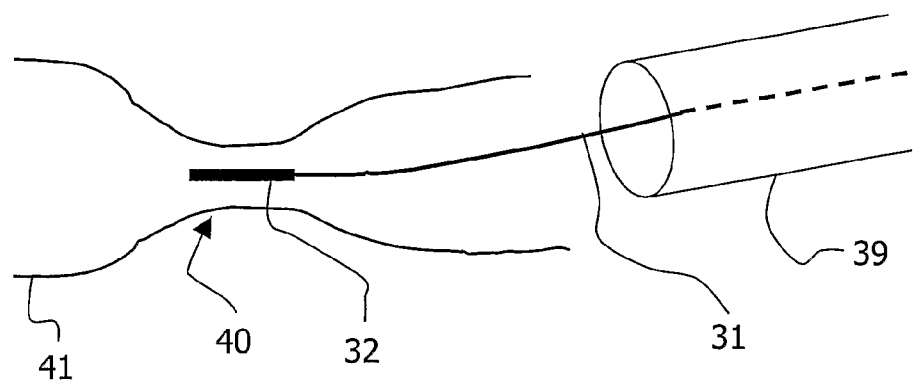
FIG. 4A to FIG. 4C illustrate the information displayed in a "Balloon Sequence"
Figure 4B:
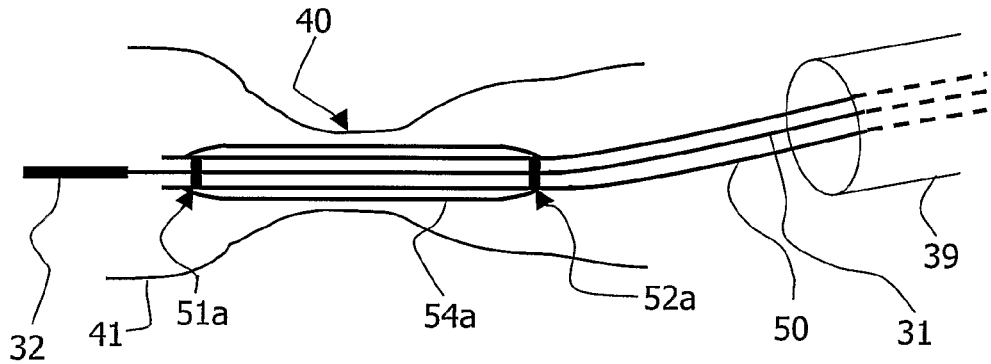
Figure 4C:
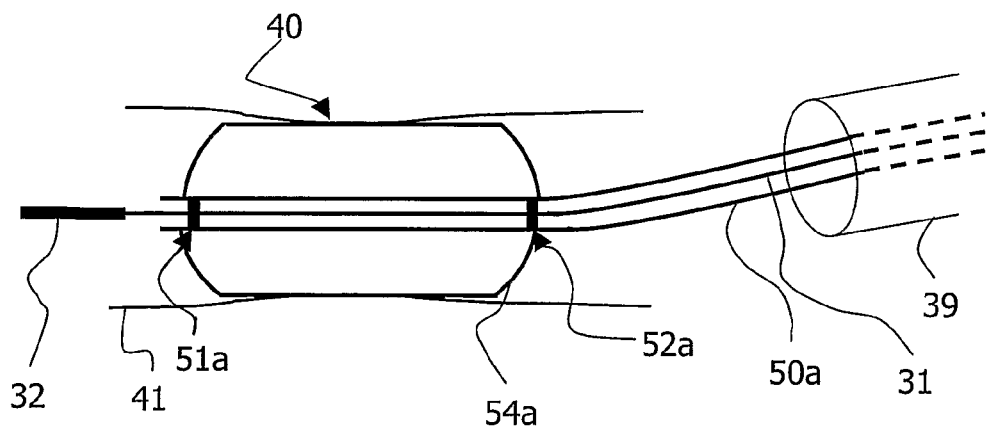

So, PTCA usually comprises several stages for enlarging a coronary at the location of a lesion called stenosis, which are described hereafter in details:

a) Referring to FIG. 4A, introduction in the coronary 41, using a catheter 39, of a thin guide-wire 31 that extends beyond the extremity of the catheter 39, and passes through the small lumen of the coronary portion 40 at the location of the stenosis.

b) Referring to FIG. 4B, introduction of a first monorail 50a, which is guided by said guide-wire 31, which passes through an opening of the monorail 50a, and which has a first balloon 54a wrapped around its extremity, without stent; and positioning said first balloon 54a in the coronary portion 40 at the stenosis location.

c) Referring to FIG. 4C, inflation of this first balloon 54a, for expanding the narrow lumen 40 of the coronary 41 at the location of the stenosis; then, removal of the first balloon 54a with the first monorail 50a. The first balloon is inflated by contrast agent.

The medical viewing system of the invention has recording means to record images during stages a) to c), thus forming the first sequence of images called "Balloon Sequence" 10, as illustrated by FIG. 1A and FIG. 1B. In the "Balloon Sequence" 10 illustrated by FIG. 1A, step c) corresponds to module 11.

Figure 5A:
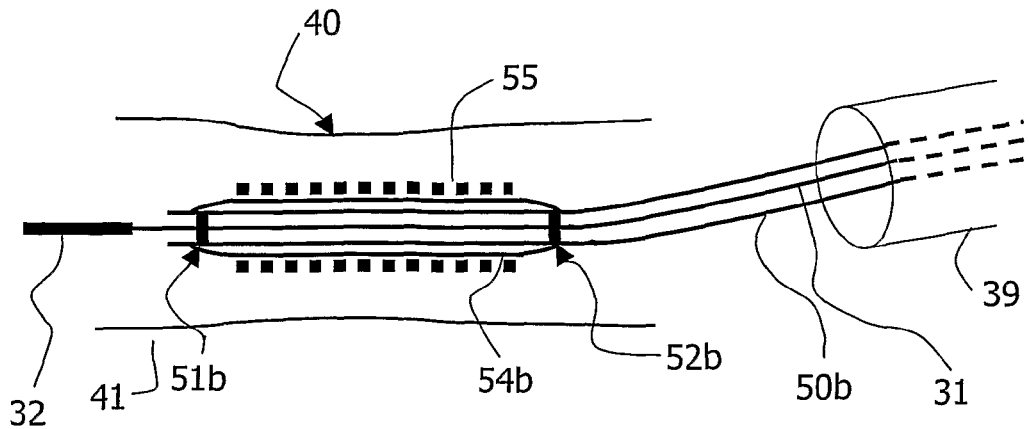
FIG. 5A to FIG. 5C illustrate the information displayed in a "Stent sequence"
Figure 5B:
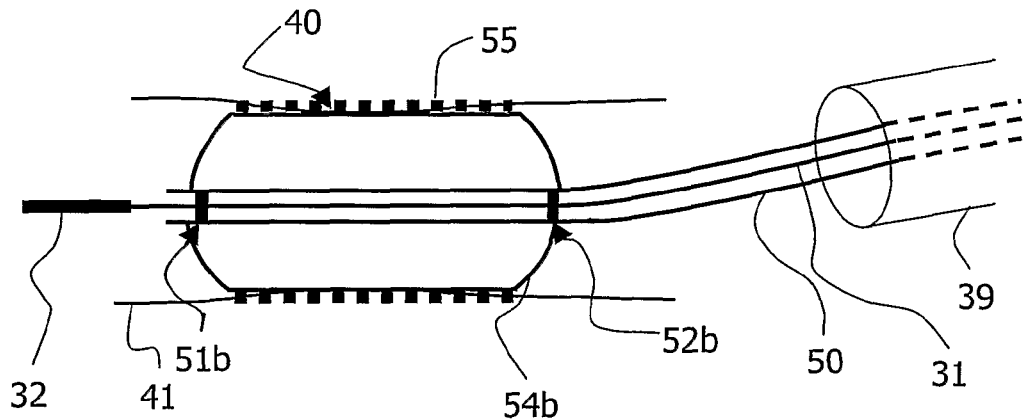
Figure 5C:
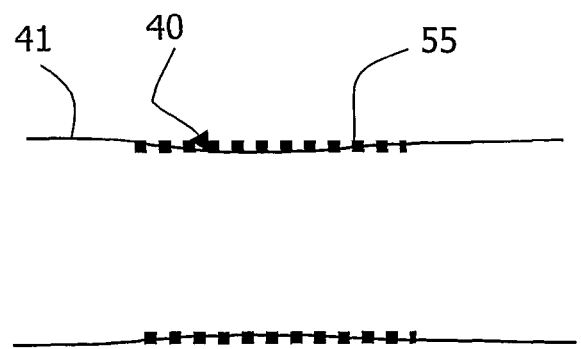

The PTCA steps recorded in "Balloon Sequence" are followed by:

d) Referring to FIG. 5A, again using the catheter 39 and the thin guide-wire 31, introduction of a second monorail 50b with a second balloon 54b wrapped around its extremity, and with a stent 55 around said second balloon 54b; and positioning said second balloon with the stent at the location of the stenosis in the previously expanded lumen 40 of the coronary 41.

e) Referring to FIG. 5B, inflation of the second balloon 54b in order to expand the coil forming the stent 55, which becomes embedded in the coronary wall.

f) The catheter may be kept in steady position inside the stent immediately after stent expansion, and with deflated balloon, during the acquisition of an image sequence called "Outcome Control Sequence", further used for performing "Outcome Control" 30 of the stent implantation.

g) Referring to FIG. 5C, after stent expansion, considering the expanded stent 55 as a permanent implant, the second balloon 54b, the second monorail 50b, the guide-wire 31 and catheter 39 are removed.

h) Next, the "Outcome Control Sequence" can be transferred to a workstation having a monitor screen for displaying images. The workstation has image processing means for off-line processing.

So, the medical viewing system of the invention has recording means to record and store images during stages d) to g), thus forming the second sequence of images called "Stent Sequence" 20, as illustrated by FIG. 1A and FIG. 1B. In the "Stent Sequence" 20 illustrated by FIG. 1A, step d) corresponds to module 21.

The images may be processed and displayed directly on-line, during PTCA, or these images may be processed and displayed off-line for "Outcome Control" 30, for instance.

The medical intervention called PTCA is difficult to carry out due to badly contrasted medical images, where the guide-wire, balloon, stent and coronary walls, which are practically radio-transparent, are hardly distinguishable on the noisy background of the fluoroscopic images and are moreover submitted to motions.

Hence, a key step of PTCA is image processing for improving stent positioning in the stenosed coronary and stent expansion in the artery walls. Dire clinical problems are associated with inadequate placement or expansion of the stent. Inadequately positioned or expanded stents can locally disrupt blood flow and cause thrombosis. The alternative to the angioplasty is a heavy intervention for bridging the stenosed part of the artery. This heavy intervention comprises opening the rib cage of the patient, which leaves much more sequels than the PTCA intervention.

Therefore, it is very important to dispose of imaging processing means for improving the visualization of the medical tools at all stages of the PTCA. Moreover it is important to minimize the duration of PTCA for minimizing patients' and doctors' irradiation. Besides, it is important to dispose of means for performing an accurate outcome control of the stent positioning.

According to the invention, an image processing means, referred to as "Stent Boosting", illustrated by means 22-25 in FIG. 1A and FIG. 1B, is used for improving medical tools visualization in the stages represented in the second image sequence called "Stent Sequence" 20 and/or in the "Outcome Control Sequence" 30. The image processing means can be applied on-line for real time image processing in the second image sequence called "Stent Sequence" 20. Or the image processing means can be applied off-line for the "Outcome Control" 30.

Figure 6A:
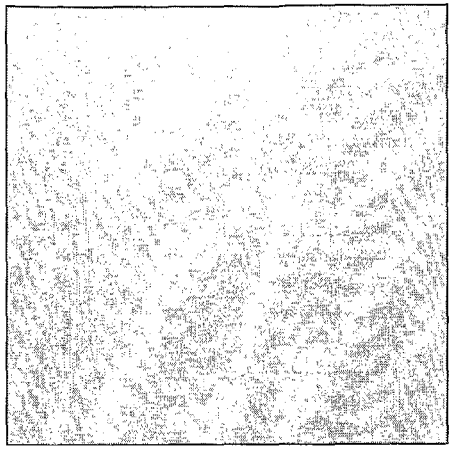
FIG. 6A shows an image of stent displayed without "Stent Boosting" and FIG. 6B shows an image of stent processed with "Stent Boosting", in an automatically defined ROI.
Figure 6B:
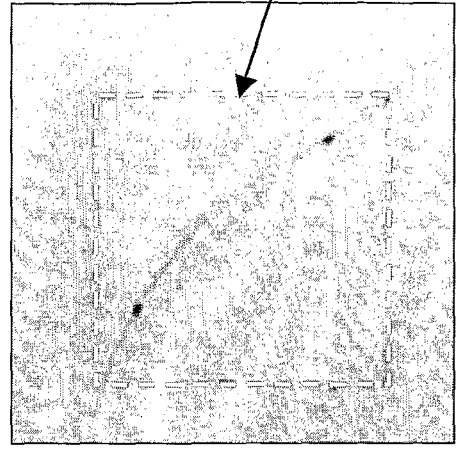

FIG. 6A shows an image of a stent in an original stent image, i.e. without "Stent Boosting" and FIG. 6B an image of a stent image enhanced by "Stent Boosting". It may be seen that "Stent Boosting" enhances greatly stent edges and improves stent visibility.

The term "Stent Boosting" refers to image processing means of feature enhancement for carrying out steps d), e) or outcome control f) of PTCA in the above cited sequences of stent images. The "Stent Boosting" image processing means can favorably work in real time, being applied directly to the system used during PTCA, for on-line improvement of feature visualization in the images of the "Stent Sequence" or still on-line, in the images of the "Outcome Control" sequence. Instead the "Stent Boosting" image processing means may be applied off-line for "Outcome Control" using a workstation.

In "Stent Sequence" or in "Outcome Control Sequence", as illustrated by FIG. 1B, the image processing means comprise registration means for balloon marker registration, including:

Means for balloon marker location, as illustrated by means 22 of FIG. 1B: The Stent Boosting means first comprise extracting means for automatic recognition of two radio-opaque markers in frames of the "Stent Sequence" 10. The markers 51b, 52b are on the catheter 50b used for placement of the stent 55.

Means for balloon marker registration, as illustrated by means 23 of FIG. 1B: The image processing means freezes the position and orientation of the markers with respect to each other at the center of the monitor screen in every frame of the image sequence and matches the position of the markers for instance to their positions in the first frame.

As illustrated by FIG. 2A, FIG. 2B, FIG. 2C, FIG. 2D and FIG. 3, the image registration comprises three basic operations that are: translation T, rotation R, and dilation or reduction $\Delta$. The direct environment, which has a fixed position with respect to the markers, including the stent, is thus frozen as well. The background, which is, however, moving from frame to frame due for example to the motion of the heart and respiration, is not frozen. Hence the background is blurred.

Figure 2A:
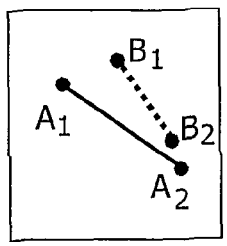
FIG. 2A to FIG. 2D illustrate marker registration.
Figure 2B:
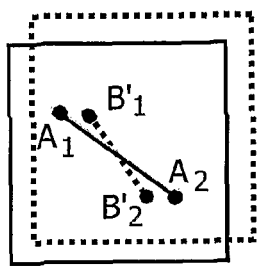
Figure 2C:
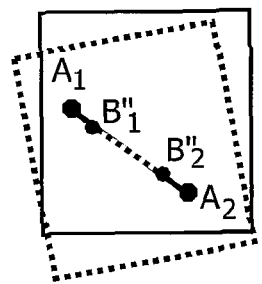
Figure 2D:
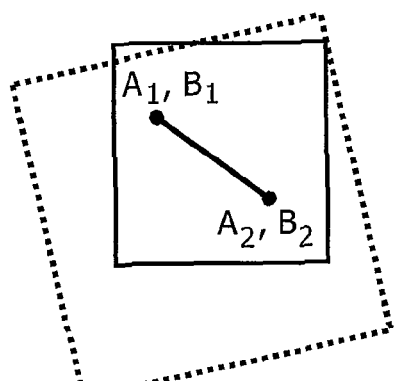
Figure 3:
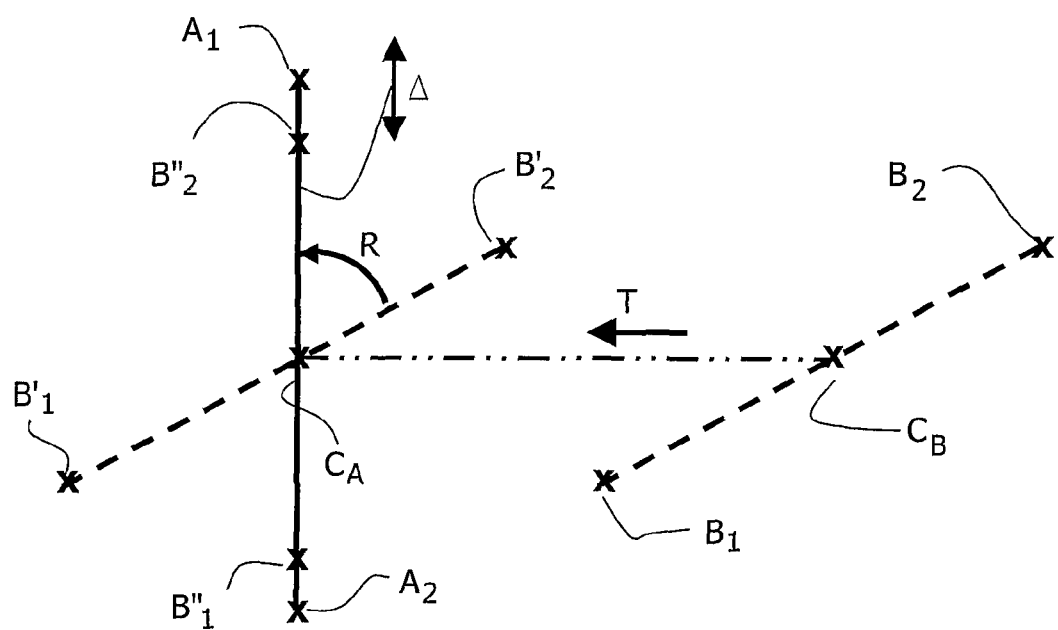
FIG. 3 illustrates operations for marker registration.

FIG. 3 shows marker location $A_1$, $A_2$ detected in a first image illustrated by FIG. 2A, and marker location $B_1$, $B_2$ detected in a second image. Translation T moves the center $C_B$ of $B_1B_2$ to the center $C_A$ of $A_1A_2$, resulting in a new position $B'_1B'_2$, as illustrated by FIG. 2B. Rotation R makes the axis of $B'_1B'_2$ coincide with the axis of $A_1A_2$, resulting in new position $B''_1B''_2$, as illustrated by FIG. 2C. Then dilation or reduction $\Delta$ registers the markers in position $A_1A_2$, as illustrated by FIG. 2D.

Averaging of the frozen frames thus leads to a much enhanced contrast of the environment of the markers, and therefore of the stent 55, whereas all structures and noise of surrounding areas in the background are smoothed out with a subsequent loss of contrast. In this way, the stent visibility is much enhanced. An example of an enhanced stent can be seen in FIG. 6B.

If "Stent Boosting" means were applied to the images without specific conditions, then said means show a drawback: this drawback is that mere Stent Boosting is not completely robust and can therefore not be fully automated. During application of Stent Boosting image processing means onto a large database of stent images, it has been observed that a certain percentage (5-10%) of markers are detected uncorrectly. Since Stent Boosting is applied to registered images, which registration is based on marker detection, Stent Boosting means may provide wrongly enhanced stent images.

One cause of poor Stent Boosting resulting images is due to misdetection of the balloon markers of reference for registration. Instead of the correct balloon markers, in the original stent images, parasitic marker-like objects, such as stitches, ECG markers etc., in the neighborhood of the actual balloon markers may be mistaken for correct balloon markers.

In order to increase the reliability of the marker extraction means, a Region Of Interest (ROI) is drawn in the original Stent Sequence of images. The ROI must be drawn in such a way that foreign, parasitic objects are outside the ROI. This ROI is of vital importance in the Stent Boosting application, in order to drastically reduce the number of false alarms during marker extraction, hence improving the results of the registration means using marker locations. A disadvantage in the phase of ROI drawing appears if the image processing means requires an explicit user interaction: that is using interactive drawing means for the user to draw the mentioned ROI.

This disadvantage can be avoided with means for automatically finding a restricted ROI, prior to actuating the actual Stent Boosting means. According to the invention, this automatic definition of the ROI is based on an automatic detection of the balloon, in the phase of balloon inflation. The basic idea for automatically finding the restricted ROI is to use the inflated "Balloon Sequence" of images, which is always recorded prior to the recording of the "Stent Sequence" of images or of the "Outcome Control" sequence of images, because the doctor needs to see the balloon expansion, to check if the stenosis is correctly dilated. Recording and storing the "Balloon Sequence" of images is a usual protocol during PTCA.

Figure 7A:
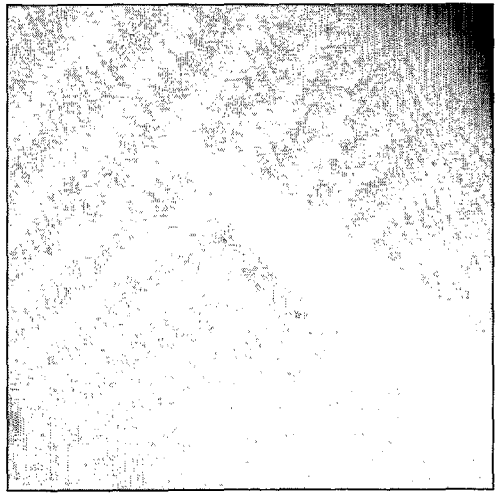
FIG. 7A shows a typical frame in a Balloon Sequence.
Figure 7B:
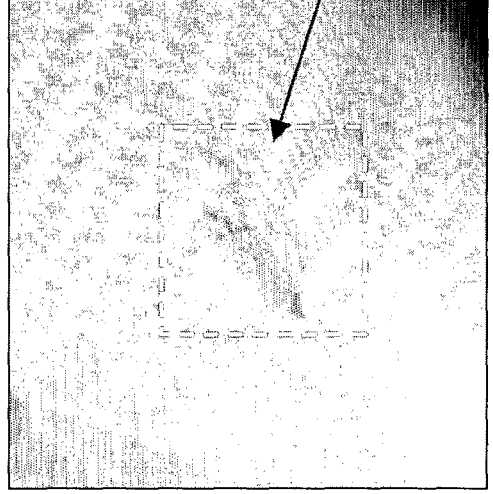
FIG. 7B is a frame showing a pixel-wise minimum region determined out of a number of frames in the "Balloon Sequence", indicating an appropriate automatic ROI, represented by a dashed square.

During the steps recorded and stored in the "Balloon Sequence", the first balloon 54a is detected. For this detection, first balloon 54a is preferably inflated with contrast agent and thus is very well visible. As illustrated by FIG. 7A, it appears like a large, contrasting dark object in the images. Since images of the "Balloon Sequence" are usually recorded in exactly the same projection as the subsequent images of the "Stent Sequence", where the second balloon 54b is now deflated inside the stent, as shown in FIG. 5A, automatic determination of the ROI on the basis of the location of the first balloon 54a, as seen in the "Balloon Sequence", is feasible and results in a ROI suitable for "Stent Boosting", as illustrated by FIG. 7B. The balloon markers 51b, 52b in the actual "Stent Sequence" will be at the same location as the balloon markers 51a, 52a of the inflated balloon in the "Balloon Sequence", provided that the operator does not change the position of the patient's table in between.

In addition, it has been found that markers could be detected, even when surrounded by contrast product. Thus, it is possible to keep track of potential marker couple candidates and to look around those candidates for balloon detection. The combination of marker couple candidate detection and balloon detection around those couples should lead to robust balloon detection.

FIG. 1A is a diagrammatic representation of the proposed means of the invention. A ROI is first estimated by means of a pre-recorded "Balloon Sequence" 10 of images during a first phase of balloon inflation 11 using contrast agent. Again it is to be noted that the contrast agent is introduced through monorail 50a and is limited to the balloon 54a. The contrast agent is not perfused in the coronary of the patient. This ROI 1 is now automatic input for the "Stent Boosting" processing means 24, illustrated by FIG. 1B. A possible procedure of "Stent Boosting" is represented by means 22-25 in FIG. 1A. The procedure of ROI automatic determination can be directly applied to the "Stent Sequence" using step e) of inflation of the balloon 54b. In this direct procedure, balloon 54b is inflated with contrast agent and used for defining the ROI, instead of balloon 54a in step c) of the "Balloon Sequence".

FIG. 7A shows a typical frame in a balloon sequence during stent placement. The balloon markers, which are important features in Stent Boosting, are visible together with the inflated balloon. FIG. 7B shows a frame representing the pixel-wise minimum region, out of a number of frames in the "Balloon Sequence". This minimum shows the union of locations of the balloon during cardiac motion. This collection of balloon positions indicates the approximate required automatic ROI, shown by the dashed square in the picture.

Extracting means that solves the problems of automatically and accurately localizing the balloons and the markers in the sequence. Once the marker location has been determined using the automatic extracting means, registering means provides registered sequence images, based on marker location. Then, enhancing means yields images with enhanced objects of interest, such as the stent. Zooming means, which are now applied to stable objects of interest in the registered images, permits an improved visualization of the regions of interest with the tools and the blood vessels in processed images.

The processed images permit of checking the position of the second balloon 54b, with the stent 55 wrapped around it, before stent expansion and permits of finally checking the expanded stent. The result of these image processing steps further permits of checking the proper expansion of the lumen of the artery after the inflation of the first balloon; and permits of checking the proper expansion of the stent after the inflation of the second balloon.

In the registered "Stent Sequence", in the ROI, the stent is enhanced by the "Stent Boosting" means. The shape and dimension of the stent is a-priori knowledge, which can be stored in memory means of the system. The boundaries of the stent are substantially parallel to the segment formed by the balloon-markers, and at a distance from this segment that can be derived from the a-priori knowledge. So, these boundaries are detected, extracted and enhanced by the enhancing means of the system known to those skilled in the art. The artery walls can be detected, extracted and enhanced by Stent Boosting in a similar manner.

The registered ROI are preferably filtered for minimizing noise. The system Stent Boosting means may comprise noise filter means. In an example, the registered ROI are integrated by averaging means applied to the intensity of the points. By this operation, the details of objects, such as vessels, which are in time concordance, are enhanced while the details of the background, which are not in time concordance, are minimized. The registered images are also preferably submitted to spatial background subtraction means of the Stent Boosting means. Background subtraction means permits of eliminating large contrasted zones and permits of again enhancing the objects of interest. The enhancing means may comprise spatial enhancement means such as ridge enhancement means. The enhancing means may also comprise temporal integration means for enhancing line-like structures and blurring the background or a combination of spatial and temporal enhancement means. The result of these image processing steps further permits of checking the proper expansion of the stent after the inflation of the second balloon.

A computer executable image processing method to be used in a system as above described has steps of processing a sequence of digital images during the medical intervention, comprising automatically extracting balloons; automatically determining the marker location; automatically defining a ROI; and processing the images to improve the visibility of the stent and/or of the coronary. The method permits of displaying the images during the medical intervention for the user to position the balloon and stent in the coronary at a specific location using the marker location information in the automatic ROI.

Figure 8:
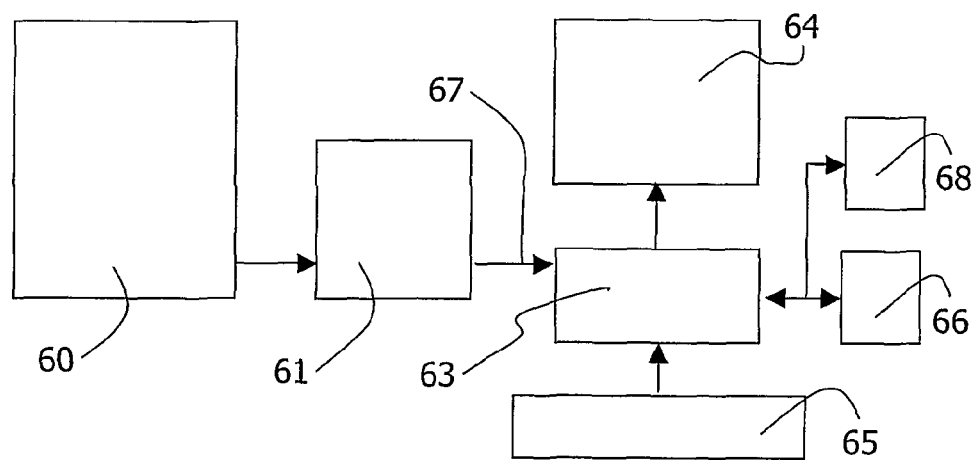
FIG. 8 is a functional block diagram of a medical examination apparatus using said system.

FIG. 8 shows a diagram of a medical examination apparatus 60. The apparatus has means 61 for acquiring digital image data of a sequence of images, and is coupled to a medical viewing system 63 as described above, for processing these data according to the processing method cited above. The medical viewing system is generally used in the intervention room or near the intervention room for processing real time images. Steps of the present method can be applied on stored medical images, for example for estimating medical parameters. The system for processing the data of the stored images is then called medical viewing station. The medical examination apparatus provides the image data by connection 67 to the system 63. The system provides processed image data to display means and/or storage means. The display means 64 may be a screen. The storage means may be a memory MEM of the system 63. Said storage means may be alternately external storage means. This image viewing system 63 may comprise a suitably programmed computer, or a special purpose processor having circuit means such as LUTs, Memories, Filters, Logic Operators, that are arranged to perform the functions of the method steps according to the invention. The system 63 may also comprise a keyboard 65 and a mouse 66. Icones may be provided on the screen to be activated by mouse-clicks, or special pushbuttons may be provided on the system, to constitute control means 68 for the user to start, to control the duration or to stop the processing means of the system at chosen stages or phases.

The invention claimed is:

1. A medical viewing system for acquiring and displaying a sequence of medical angiograms representing an artery with a balloon, moving in the artery, this system comprising processing means including:
    extracting means for automatically extracting balloon image data of the balloon from the sequence of medical angiograms in a phase of balloon expansion, wherein the balloon is inflated with contrast agent;
    computing means for automatically defining and storing coordinates of a Region of Interest (ROI) based on the automatically extracted balloon image data of the balloon inflated with contrast agent, said Region of Interest being defined as a limited region around an automatically extracted expanded balloon zone of a corresponding image of the sequence of medical angiograms;
    processing means for using an automatically previously defined and stored coordinates in order to apply the previously defined ROI to another sequence of medical angiograms, for extracting balloon markers associated to a deflated balloon, in another phase of stent implantation in the artery, where a stent is wrapped around the deflated balloon, and for registering the ROI based on the markers location; and
    display means for displaying the images of the sequence of medical angiograms.

2. The medical viewing system of claim 1, wherein the balloon is coupled to balloon markers, comprising processing means including:
    detecting means for detecting balloon marker candidates;
    detecting means to keep track of the balloon marker candidates and to look around those candidates for further balloon image data detection based on the location of the marker candidates, and
    extracting means for automatically extracting the detected balloon image data.

3. The medical viewing system of claim 1, comprising processing means for using the automatically previously defined and stored coordinates in order to apply the previously defined ROI to a sequence of angiograms representing a balloon, for extracting balloon markers associated to the balloon, and for registering the ROI based on the markers location.

4. A medical viewing system for acquiring and displaying a sequence of medical angiograms representing an artery with a balloon, moving in the artery, this system comprising processing means including:
    extracting means for automatically extracting balloon image data in a phase of balloon expansion, and computing means for automatically defining and storing coordinates of a Region of Interest (ROI) based on the expanded balloon image data, said Region of Interest being defined around an expanded balloon zone of a corresponding image,
    display means for displaying the images, further comprising processing means for using the automatically previously defined and stored coordinates in order to apply the previously defined ROI to another sequence of images, for extracting balloon markers associated to a deflated balloon, in another phase of stent implantation in the artery, where a stent is wrapped around the deflated balloon, and for registering the ROI based on the markers location.

5. The medical viewing system of claim 4, further comprising processing means for enhancing the stent.

6. The system of claim 5, wherein the enhancing means comprises ridge enhancement means and temporal integration means for enhancing line-like structures and blurring the background.

7. The system of claim 5, wherein the enhancing means comprises:
zooming means for zooming on the Region Of Interest.

8. The system of claim 1, comprising processing means:
for storing one or several sequences to be processed.

9. A medical viewing system for acquiring and displaying a sequence of medical anqiograms representing an artery with a balloon, moving in the artery, this system comprising processing means including:
extracting means for automatically extracting balloon image data in a phase of balloon expansion, and computing means for automatically defining and storing coordinates of a Region of Interest (ROI) based on the expanded balloon image data, said Region of Interest being defined around an expanded balloon zone of a corresponding image,
display means for displaying the images, further comprising processing means:
for storing one or several sequences to be processed, and for storing a first sequence representing a balloon in a phase of inflation for automatically defining a ROI, and for displaying a second sequence representing a deflated balloon for applying the previously defined ROI, for balloon marker detection and for ROI registration based on the markers in the ROI.

10. An image processing method to be used in a system as claimed in claim 1.

11. A device comprising a suitably programmed computer or a special purpose processor having circuit means, which are arranged to process images, to be used in a system as claimed in claim 1.

12. A non-transitory computer-readable medium embodied with a computer program comprising a set of instructions executable by a processor for carrying out an image processing method to be used in a system as claimed in claim 1.

13. A medical examination apparatus having means for acquiring a sequence of medical images and having a system for processing and for displaying said sequence of images according to claim 1.

14. The medical viewing system of claim 1, further comprising processing means for enhancing the stent.

15. The system of claim 14, further wherein the enhancing means comprises ridge enhancement means and temporal integration means for enhancing line-like structures and blurring the background.

16. The system of claim 14, further wherein the enhancing means comprises:
zooming means for zooming on the Region Of Interest.

17. The system of claim 8, further comprising processing means for storing a first sequence representing a balloon in a phase of inflation for automatically defining a ROI, and for displaying a second sequence representing a deflated balloon for applying the previously defined ROI, for balloon marker detection and for ROI registration based on the markers in the ROI.

* * * * *